(12) United States Patent
Kanakkanatt et al.

(10) Patent No.: US 9,387,273 B2
(45) Date of Patent: *Jul. 12, 2016

(54) LIQUID-ACTIVATED COLOR CHANGE INK AND METHODS OF USE

(71) Applicant: The Procter & Gamble Company, Cincinnati, OH (US)

(72) Inventors: Sebastian V. Kanakkanatt, Akron, OH (US); Santosh B. Kanakkanatt, Akron, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 115 days.

This patent is subject to a terminal disclaimer.

(21) Appl. No.: 14/037,414

(22) Filed: Sep. 26, 2013

(65) Prior Publication Data

US 2014/0088534 A1 Mar. 27, 2014

Related U.S. Application Data

(60) Provisional application No. 61/705,861, filed on Sep. 26, 2012.

(51) Int. Cl.
| | |
|---|---|
| *C09D 11/50* | (2014.01) |
| *A61L 15/56* | (2006.01) |
| *A61L 15/20* | (2006.01) |

(52) U.S. Cl.
CPC .................. *A61L 15/56* (2013.01); *A61L 15/20* (2013.01); *C09D 11/50* (2013.01)

(58) Field of Classification Search
CPC ....................................................... C09D 11/50
See application file for complete search history.

(56) References Cited

U.S. PATENT DOCUMENTS

| | | |
|---|---|---|
| 3,675,654 A | 7/1972 | Baker et al. |
| 3,759,261 A | 9/1973 | Wang |
| 3,952,746 A | 4/1976 | Summers |
| 4,022,211 A | 5/1977 | Timmons et al. |
| 4,150,570 A | 4/1979 | Fuller |
| 4,192,311 A | 3/1980 | Felfoldi |
| 4,231,370 A | 11/1980 | Mroz et al. |
| 4,327,731 A | 5/1982 | Powell |
| 4,699,885 A | 10/1987 | Melpolder et al. |
| 4,931,051 A | 6/1990 | Castello |
| 4,990,284 A | 2/1991 | Lauterbach et al. |
| 5,290,516 A | 3/1994 | Greco et al. |
| 5,435,010 A | 7/1995 | May |
| 5,766,312 A | 6/1998 | Furhmann et al. |
| 5,858,788 A | 1/1999 | Habenstein |
| 6,114,170 A | 9/2000 | Habenstein |
| 6,572,694 B2 | 6/2003 | Towe |
| 6,653,522 B1 | 11/2003 | Blumenthal et al. |

(Continued)

FOREIGN PATENT DOCUMENTS

| | | |
|---|---|---|
| JP | 2004-285191 A | 10/2004 |
| JP | 2009-273417 | 11/2009 |
| WO | WO 0236177 A2 | 5/2002 |

OTHER PUBLICATIONS

International Search Report, PCT/US2013/061858, mailed Jan. 8, 2014, 9 pages.

*Primary Examiner* — Veronica F Faison
(74) *Attorney, Agent, or Firm* — Kathleen Y. Carter

(57) ABSTRACT

Liquid activated ink formulations comprising a liquid activated dye, a hydrochromic ionic compound, an opacifier, and a solvent.

17 Claims, 2 Drawing Sheets

(56) References Cited

U.S. PATENT DOCUMENTS

| | | |
|---|---|---|
| 6,655,315 B1 | 12/2003 | Gattiglia |
| 6,772,708 B2 * | 8/2004 | Klofta ............... A61F 13/42 116/200 |
| 6,904,865 B2 | 6/2005 | Klofta et al. |
| 7,159,532 B2 | 1/2007 | Klofta et al. |
| 8,198,504 B2 | 6/2012 | Glaug |
| 8,247,237 B2 | 8/2012 | Moreton |
| 8,502,010 B2 | 8/2013 | McKiernan et al. |
| 2003/0235654 A1 * | 12/2003 | Puntambekar ............ A61L 2/28 427/378 |
| 2005/0276937 A1 | 12/2005 | Kosth |
| 2010/0004613 A1 | 1/2010 | Cohen |
| 2010/0012017 A1 | 1/2010 | Miller |
| 2010/0030173 A1 | 2/2010 | Song et al. |
| 2010/0262099 A1 | 10/2010 | Klofta |
| 2010/0262100 A1 | 10/2010 | Klofta |
| 2011/0015597 A1 | 1/2011 | Gil et al. |
| 2011/0015599 A1 | 1/2011 | Song |
| 2011/0137274 A1 | 6/2011 | Klofta |
| 2011/0144603 A1 | 6/2011 | Song |
| 2012/0143160 A1 | 6/2012 | Song |
| 2012/0144906 A1 | 6/2012 | Knyrim |
| 2012/0308787 A1 | 12/2012 | Kozee |
| 2013/0066289 A1 * | 3/2013 | Song ................... A61L 15/56 604/361 |

* cited by examiner

LIQUID-ACTIVATED COLOR CHANGE INK AND METHODS OF USE

BACKGROUND OF THE INVENTION

The present invention is in the field of wetness/fluid indicators. More specifically this invention relates to wetness/fluid indicating ink which indicates the presence of fluid by color change. This is especially useful in diapers, wound dressings, home construction uses, and other areas where it is desired to detect the presence of fluids.

Prior art discloses several methods for indicating wetness with a color change. U.S. Pat. No. 4,231,370 to Mroz et al. discloses a pH change/color change wetness indicator which is a solid mixture dispersed in an adhesive. U.S. Pat. No. 4,022,211 to Timmons et al. discloses a water soluble coloring agent which is visible when a diaper is dry, but which disappears when a diaper becomes wet. U.S. Pat. No. 3,952,746 to Summers discloses the use of humidity indicator paper mounted on an absorbent area of the diaper. U.S. Pat. No. 4,327,731 to Powell discloses moisture activated enzymatic systems and chromogens or pigment producing agents used as wetness detectors. U.S. Pat. No. 3,759,261 to Wang and U.S. Pat. No. 4,192,311 to Felfoldi disclose masked color layers which become visible when intervening layers become wet. U.S. Pat. No. 4,931,051 to Castello discloses a wetness indicator that includes a solid hydratable salt as an active ingredient to detect and visually signal the presence of water.

Many pH indicators may be unreliable. The other methods disclosed are also complicated to manufacture, as most require binding agents of some kind, and/or several manufacturing steps for implementation into a finished product A simple, non-toxic wetness/fluid indicator is desired which would be able to be utilized with minimal manufacturing steps, for detection of almost any type of fluid.

SUMMARY

The liquid activated ink formulations which are utilized in this invention are comprised of a liquid activated dye; a hydrochromic ionic compound; an opacifier; and a solvent. The liquid activated die is water soluble and changes color upon coming in contact with liquid. This liquid activated ink may be useful in many applications including a wetness indicator on diapers, wound dressings, construction, feminine hygiene, and many others.

DETAILED DESCRIPTION

Figure 1:
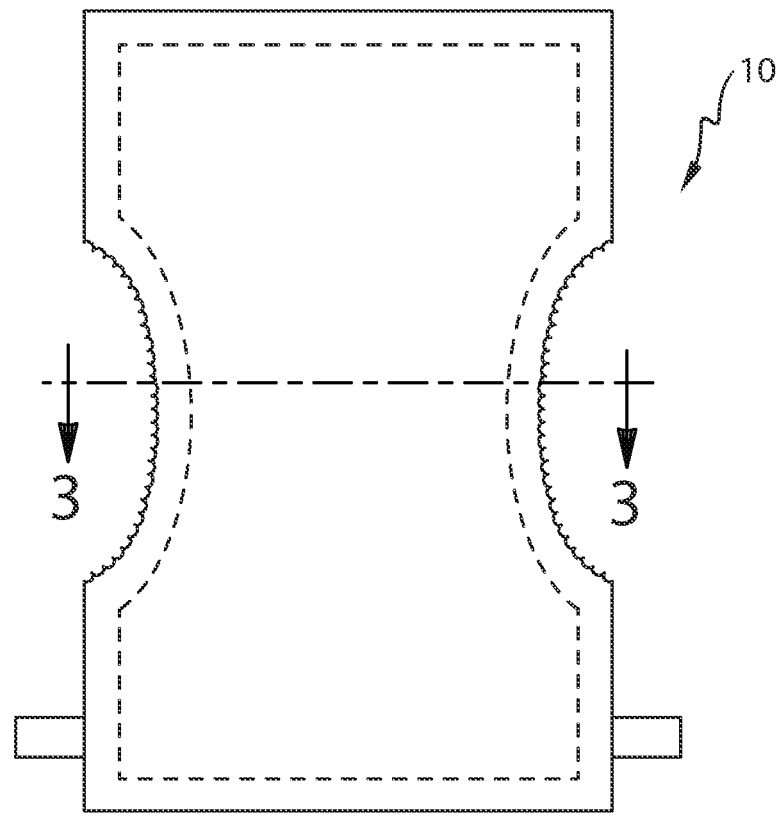
FIG. 1 is an top view of a diaper according to an aspect of the invention.

Various aspects of the invention are presented in FIGS. 1-4 which are not drawn to scale and in which like components are numbered alike.

The liquid activated ink formulations which are utilized in this invention are comprised of a liquid activated dye; a hydrochromic ionic compound; an opacifier; and a solvent. The liquid activated die is liquid soluble and changes color upon coming in contact with water. Some representative examples of liquid activated dyes that can be used in the practice of this invention include: Malachite green, brilliant green, crystal violet, erythrosine B, methyl green, methyl violet 2D, picric acid, naphthol yellow S, quinaldine red, eosine Y, metanil yellow, m-cresol purple, thymol blue, xylenol blue, basis fuchsin, eosin B, 4-p-aminophenol(azo)benzenesulphonic acid-sodium salt, cresol red, martius yellow, phloxine B, methyl yellow, bromophenol blue, congo red, methyl orange, bromochlorophenol blue WS, ethyl orange, flourocene WS, bromocresol green, chrysoidine, methyl red sodium salt, alizarine red S—H2O, cochineal, chlorophenol red, bromocresol purple, 4-naphtha, alizarin, nitrazine yellow, bromothymol blue, brilliant yellow, neutral red, rosalic acid, phenol red, 3-nitro phenol, orange II, phenolphthalein, o-cresolphthalein, nile blue A, thymolphthalein, aniline blue WS, alizarine yellow GG, mordant orange, tropaolin O, orange G, acid fuchsin, thiazol yellow G, and indigo carmine.

The hydrochromic ionic compound is typically a reactive ionic compound, such as an ionizing salt. Some representative examples of hydrochromic ionic compounds that can be employed in the practice of this invention include: lithium hydrogen sulfate, lithium hydrogen carbonate, potassium hydrogen sulfate, potassium hydrogen carbonate, rubidium hydrogen sulfate, rubidium hydrogen carbonate, cesium hydrogen sulfate, cesium hydrogen carbonate, sodium hydrogen sulfate, sodium hydrogen carbonate, cesium hydroxide, lithium hydroxide, potassium hydroxide, calcium hydroxide, magnesium hydroxide, sodium thiosulfate penta hydrate, sodium hydroxide, rubidium hydroxide, cobalt chloride, cobalt nitrate, copper sulpate copper nitrate, iron (II) sulfate, iron (III) sulfate, iron (II) chloride, and iron (III) chloride.

The opacifiers that can be utilized in the liquid activated ink formulations of this invention can be porosigens or antiporosigens and are typically white powders when they are in the form of dry solids (before being incorporated into the ink formulation). In the cases where the opacifiers act as porosigens they allow for liquid transmission through coatings which are applied to a substrate, such as a coating which is printed on the outer layer of a diaper. In other words, the porosigen is a compound which allows for liquid to be transmitted through it which facilitates liquid transmission throughout the coating. In the case of antiporosigens liquid transmission is attained by virtue of liquid permeable interstices which are formed in proximity to the antiporosigens by virtue of disrupting the structure of liquid barrier materials. In other words, the antiporosigens cause holes to be present in the dry coating structure which are of a size and structure which allows for liquid to flow through the coating. Some representative examples of opacifiers that can be utilized include titanium dioxide, calcium carbonate, calcium hydroxide, sodium silicate, potassium silicate, silica, starch, ethocell, methocell, barium carbonate, barium silicate, calcium silicate, aluminum silicate, aluminum hydroxide, and aluminum oxide.

The solvent utilized in the liquid activated ink formulation is typically a polar solvent, such as an aqueous solvent. The solvent will normally be water or an aqueous solution of one or more water soluble agents in water. For example, a glycol or an alcohol, such as methanol, ethanol, or isopropyl alcohol, or agents which facilitate or accelerate film formation can be included in the solvent.

The liquid activated ink formulation is normally prepared by simply mixing the liquid activated dye, the hydrochromic ionic compound and the opacifier into the solvent. The desired components of the liquid activated ink formulation can be mixed together using conventional means using adequate shearing forces to attain an essentially homogeneous mixture. The liquid activated dye, the hydrochromic ionic compound and the opacifier will be incorporated into the solvent at levels which are adequate to make a liquid activated ink formulation having desired characteristics. For instance, the liquid activated ink formulation will be capable of being coated onto a substrate, such as by a printing process, and upon drying will adhere to the surface of the substrate. The liquid activated ink formulation of this invention can be printed onto paper, non-woven fabric, woven fabric, plastic or other surfaces by silk screen printing, flexo-printing, by application with a Myers rod, or by other suitable techniques. After drying on the substrate, the ink formulation will change color on exposure to water. The coating will preferably change to a blue or purple color on exposure to water.

The liquid activated dye will normally be included in the liquid activated ink formulation at a level which is within the range of about 0.05 weight percent to about 20 weight percent and will generally be incorporated into the liquid activated dye at a level which is within the range of about 0.1 weight percent to about 15 weight percent, based upon the total weight of the liquid activated ink formulation. The liquid activated dye will typically be included in the liquid activated ink formulation at a level which is within the range of about 0.5 weight percent to about 10 weight percent and will preferably be incorporated into the liquid activated dye at a level which is within the range of about 1 weight percent to about 5 weight percent.

The hydrochromic ionic compound will normally be included in the liquid activated ink formulation at a level which is within the range of about 0.05 weight percent to about 35 weight percent and will generally be incorporated into the liquid activated dye at a level which is within the range of about 1 weight percent to about 30 weight percent, based upon the total weight of the liquid activated ink formulation. The hydrochromic ionic compound will typically be included in the liquid activated ink formulation at a level which is within the range of about 10 weight percent to about 30 weight percent and will preferably be incorporated into the liquid activated dye at a level which is within the range of about 15 weight percent to about 25 weight percent.

The opacifier will normally be included in the liquid activated ink formulation at a level which is within the range of about 5 weight percent to about 55 weight percent and will generally be incorporated into the liquid activated dye at a level which is within the range of about 10 weight percent to about 50 weight percent, based upon the total weight of the liquid activated ink formulation. The opacifier will typically be included in the liquid activated ink formulation at a level which is within the range of about 20 weight percent to about 45 weight percent and will preferably be incorporated into the liquid activated dye at a level which is within the range of about 30 weight percent to about 40 weight percent

EXAMPLES

This invention is illustrated by the following examples which are merely for the purpose of illustration and are not to be regarded as limiting the scope of the invention or the manner in which it can be practiced. Unless specifically indicated otherwise, parts and percentages are given by weight.

Example 1

In this experiment a liquid activated ink formulation was prepared by adding 3.0 parts of bromochlorophenol blue WS, 20 parts of sodium hydrogen carbonate, and 35 parts of aluminum silicate into 42 parts of water. This aqueous composition was mixed by stirring until a homogeneous solution was attained to produce the liquid activated ink formulation.

Example 2

The liquid activated ink formulation made by the procedure delineated in Example 1 was printed onto a paper substrate using a Myers rod. The liquid activated ink formulation was allowed to dry and exhibited good adhesion to the substrate. After drying the coated substrate was of a generally white color.

Water was applied to the coated substrate and it immediately turned to a brilliant blue color. Accordingly, the ink formulation which was coated onto the paper substrate reacted to the presence of water by changing from a white color into an easily detectable blue color.

While certain representative embodiments and details have been shown for the purpose of illustrating the subject invention, it will be apparent to those skilled in this art that various changes and modifications can be made therein without departing from the scope of the subject invention.

Methods of Use:

According to an aspect of the invention, a disposable diaper 10 has a liquid permeable topsheet 12, a liquid impermeable backsheet 14, a liquid absorbent core 16 disposed between the topsheet 12 and the backsheet 14 and further comprises a liquid indicator 20. The liquid indicator 20 comprises a coating 18 of liquid indicating ink disposed on the backsheet 14, between the backsheet 14 and the absorbent core 16, such that it is visually revealed when the coating 18 is wetted with body fluids. The liquid indicating ink is the liquid activated ink as described above. This liquid indicator may change color entirely when in contact with liquid, or may change noticeable shades of color, or may change from an almost white (so as it appears that there is no ink there) to a color.

In prior art, there were many steps necessary for achieving liquid indicating diapers. Besides the diaper backsheet, topsheet, and absorbent core, prior art also needed a covering layer to keep the ink in place, a surfactant, a binding agent for binding the liquid indicator to the backsheet, and/or other items. Further, the ink used in prior art required a separate layer, such as maybe the ink being printed on a tissue paper or the like, and then the tissue paper being placed/adhered to the backsheet.

Prior art also required surfactants for operation of the wetness indicating diapers. The present invention can work without surfactants, although one or more surfactants may still be used.

Figure 2:
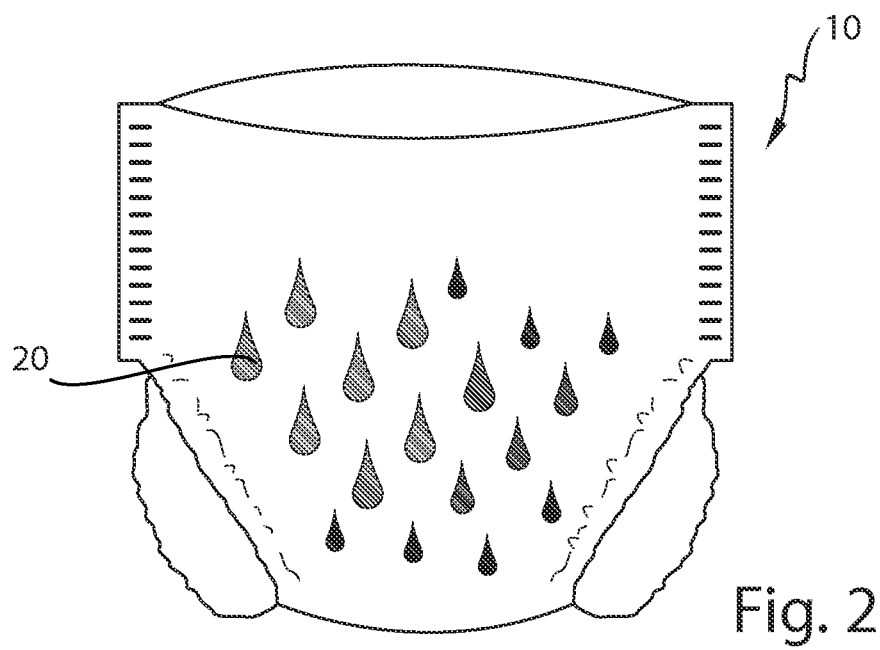
FIG. 2 is a front view of a diaper according to an aspect of the invention.
Figure 3:
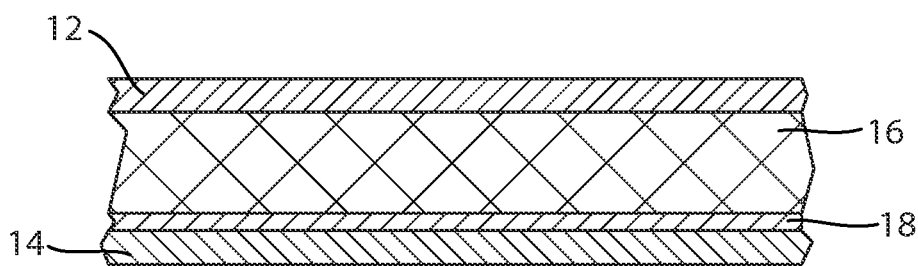
FIG. 3 is a cross section of diaper of FIG. 1 according to an aspect of the invention.
Figure 4:
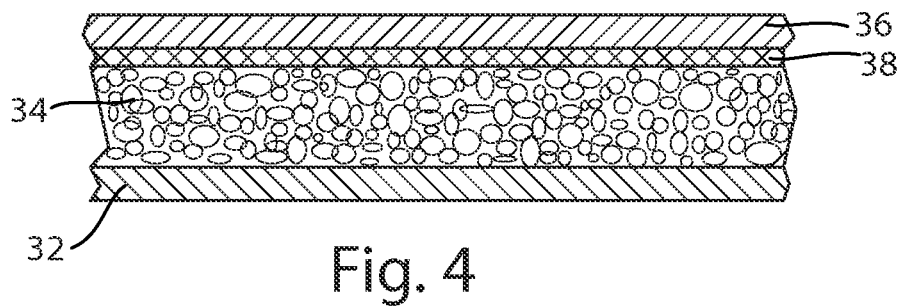
FIG. 4 is a cross section of a wound dressing according to an aspect of the invention.

In the present invention, the liquid indicating ink may be printed directly on the backsheet 14, with no binding agent, thus eliminating the need for extra layers, binders, covering layers and the like, and greatly simplifying the manufacture of liquid indicating diapers. Because of the ease of manufacture by simply printing the liquid indicator on the diaper, the liquid indicator may be printed in any way desired, such as words, shapes, numbers etc. FIG. 2 shows just one example of how the diaper may appear when wet, wherein the liquid indicator 20 is printed in a raindrop pattern which is visible when wet.

This liquid indicating ink lends itself to many other uses, such as use in wound dressings. According to an aspect of the invention, a wound dressing 30 comprises a contact layer 32, an absorbent dressing layer 34, and an outer layer 36, and further comprises a liquid indicator 40, comprising a coating 38 of liquid indicating ink wherein the liquid indicator 40 is disposed on the outer layer 36, between the outer layer 36 and the absorbent dressing layer 34. The liquid indicating ink is the liquid activated ink as described above. This liquid indicator may change color entirely when in contact with liquid, or may change noticeable shades of color, or may change from an almost white (so as it appears that there is no ink there) to a color. The outer layer 36 should be transparent or translucent enough such that this color change is visible through the outer layer 36. Thus when the wound seeps through the absorbent dressing layer to the outer layer, the color change would indicate it is time to change the dressing. Further, the liquid indicating ink could be printed only around the edges of the wound dressing to visibly indicate when the wound is seeping towards the edges of the dressing.

According to a further aspect of the invention, this liquid indicating ink may be used in construction to indicate leaks or moisture. For example, this ink could be printed on pipe tape, such that during use, if a pipe was leaking, the color change would so indicate. Further this ink could be used in insulating materials, such as pipe insulating materials. Since a pipe cannot be seen when insulated, it is difficult to determine if a pipe is leaking, or where it is leaking If the liquid indicating ink was used in pipe insulation material, then color change would indicate a leak, and its location.

Further, this liquid indicating ink can be made such that the color change is temporary, or permanent—thus if it is temporary, if a pipe with color changing insulating material is accidently exposed to liquid, through a spill for example, when the spill dries, the color would return, and the liquid indicating ink would not have lost its usefulness.

There are many other uses in construction, such as printing on gypsum board paper, which could indicate a leak, or moisture behind walls. As a further example, it could be used in manufacture of dropped ceiling panels, to indicate leaks or moisture above the dropped ceiling.

These are just a few of the example of the usefulness of this liquid indicating ink, and are not meant as an exhaustive list, as it will be apparent to those skilled in this art that various changes and modifications can be made therein without departing from the scope of the subject invention.

What is claimed is:

1. liquid activated ink formulation comprising: (A) a liquid activated dye, wherein the liquid activated dye is water soluble; (B) a hydrochromic ionic compound;
   (C) from about 20% to about 45% by weight an opacifier; and (D) a solvent.

2. The liquid activated ink formulation as specified in claim 1 wherein the opacifier is a porosigen.

3. The liquid activated ink formulation as specified in claim 1 wherein the hydrochromic ionic compound is an ionizing salt which changes color on exposure to water.

4. The liquid activated ink formulation as specified in claim 1 wherein the liquid activated dye is selected from the group consisting of Malachite green, brilliant green, crystal violet, erythrosine B, methyl green, methyl violet 2D, picric acid, naphthol yellow S, quinaldine red, eosine Y, metanil yellow, m-cresol purple, thymol blue, xylenol blue, basis fuchsin, eosin B, 4-p-aminophenol(azo)benzenesulphonic acid-sodium salt, cresol red, martius yellow, phloxine B, methyl yellow, bromophenol blue, congo red, methyl orange, bromochlorophenol blue WS, ethyl orange, flourocene WS, bromocresol green, chrysoidine, methyl red sodium salt, alizarine red S—H2O, cochineal, chlorophenol red, bromocresol purple, 4-naphtha, alizarin, nitrazine yellow, bromothymol blue, brilliant yellow, neutral red, rosalic acid, phenol red, 3-nitro phenol, orange II, phenolphthalein, o-cresolphthalein, nile blue A, thymolphthalein, aniline blue WS, alizarine yellow GG, mordant orange, tropaolin O, orange G, acid fuchsin, thiazol yellow G, and indigo carmine.

5. The liquid activated ink formulation as specified in claim 1 wherein the hydrochromic ionic compound is selected from the group consisting of lithium hydrogen sulfate, lithium hydrogen carbonate, potassium hydrogen sulfate, potassium hydrogen carbonate, rubidium hydrogen sulfate, rubidium hydrogen carbonate, cesium hydrogen sulfate, cesium hydrogen carbonate, sodium hydrogen sulfate, sodium hydrogen carbonate, cesium hydroxide, lithium hydroxide, potassium hydroxide, calcium hydroxide, magnesium hydroxide, sodium thiosulfate penta hydrate, sodium hydroxide, rubidium hydroxide, cobalt chloride, cobalt nitrate, copper sulpate copper nitrate, iron (II) sulfate, iron (III) sulfate, iron (II)chloride, and iron (III) chloride.

6. The liquid activated ink formulation as specified in claim 1 wherein the opacifier is selected from the group consisting of titanium dioxide, calcium carbonate, calcium hydroxide, sodium silicate, potassium silicate, silica, starch, ethocell, methocell, barium carbonate, barium silicate, calcium silicate, aluminum silicate, aluminum hydroxide, and aluminum oxide.

7. The liquid activated ink formulation as specified in claim 1 wherein the a liquid activated dye is present in the liquid activated ink formulation in an amount which is within the range of about 0.05 weight percent to about 20 weight percent, wherein the hydrochromic ionic compound is present in the liquid activated ink formulation in an amount which is within the range of about 0.05 weight percent to about 35 weight percent, and wherein the solvent is present in the liquid activated ink formulation in an amount which is within the range of about 5 weight percent to about 55 weight percent, based upon the total weight of the liquid activated ink formulation.

8. The liquid activated ink formulation as specified in claim 1 wherein the liquid activated dye is present in the liquid activated ink formulation in an amount which is within the range of about 0.1 weight percent to about 15 weight percent, wherein the hydrochromic ionic compound is present in the liquid activated ink formulation in an amount which is within the range of about 1 weight percent to about 30 weight percent, and wherein the solvent is present in the liquid activated ink formulation in an amount which is within the range of about 15 weight percent to about 50 weight percent, based upon the total weight of the liquid activated ink formulation.

9. The liquid activated ink formulation as specified in claim 1 wherein the liquid activated dye is present in the liquid activated ink formulation in an amount which is within the range of about 0.5 weight percent to about 10 weight percent, wherein the hydrochromic ionic compound is present in the liquid activated ink formulation in an amount which is within the range of about 10 weight percent to about 30 weight percent, and wherein the solvent is present in the liquid activated ink formulation in an amount which is within the range of about 25 weight percent to about 50 weight percent, based upon the total weight of the liquid activated ink formulation.

10. The liquid activated ink formulation as specified in claim 1 wherein the liquid activated dye is present in the liquid activated ink formulation in an amount which is within the range of about 1 weight percent to about 5 weight percent, wherein the hydrochromic ionic compound is present in the liquid activated ink formulation in an amount which is within the range of about 15 weight percent to about 25 weight percent, wherein the opacifier is present in the liquid activated ink formulation in an amount which is within the range of about 30 weight percent to about 40 weight percent, and wherein the solvent is present in the liquid activated ink formulation in an amount which is within the range of about 35 weight percent to about 45 weight percent, based upon the total weight of the liquid activated ink formulation.

11. The liquid activated ink formulation as specified in claim 1 wherein the solvent is an aqueous solvent.

12. The liquid activated ink formulation as specified in claim 1 wherein the solvent is water.

13. The liquid activated ink formulation as specified in claim 1 wherein the opacifier is in the form of a white particles.

14. The liquid activated ink formulation as specified in claim 1 wherein the opacifier is aluminum silicate.

15. The liquid activated ink formulation as specified in claim 12 wherein the liquid activated dye is bromochlorophenol blue WS.

16. The liquid activated ink formulation as specified in claim 12 wherein the hydrochromic ionic compound is sodium hydrogen carbonate.

17. The liquid activated ink formulation as specified in claim 1 wherein the opacifier is aluminum silicate, wherein the liquid activated dye is bromochlorophenol blue WS, wherein the hydrochromic ionic compound is sodium hydrogen carbonate, wherein the solvent is water, wherein the aluminum silicate is in the form of a white particles, wherein the bromochlorophenol blue WS is present in the liquid activated ink formulation in an amount which is within the range of about 1 weight percent to about 5 weight percent, wherein the sodium hydrogen carbonate is present in the liquid activated ink formulation in an amount which is within the range of about 15 weight percent to about 25 weight percent, wherein the aluminum silicate is present in the liquid activated ink formulation in an amount which is within the range of about 30 weight percent to about 40 weight percent, and wherein the water is present in the liquid activated ink formulation in an amount which is within the range of about 35 weight percent to about 45 weight percent, based upon the total weight of the liquid activated ink formulation.

\* \* \* \* \*